United States Patent
Højbjerg et al.

(10) Patent No.: US 8,303,638 B2
(45) Date of Patent: Nov. 6, 2012

(54) HEAT CUSHION

(75) Inventors: Jens Harder Højbjerg, Hvidovre (DK); Jan Bertholdt Hansen, Espergærde (DK)

(73) Assignee: Jens Harder Hojbjerg, Hvidovre (DK)

( * ) Notice: Subject to any disclaimer, the term of this patent is extended or adjusted under 35 U.S.C. 154(b) by 851 days.

(21) Appl. No.: 12/065,382

(22) PCT Filed: Aug. 30, 2006

(86) PCT No.: PCT/DK2006/000466
§ 371 (c)(1), (2), (4) Date: Aug. 5, 2008

(87) PCT Pub. No.: WO2007/025543
PCT Pub. Date: Mar. 8, 2007

(65) Prior Publication Data
US 2009/0157154 A1    Jun. 18, 2009

(30) Foreign Application Priority Data

Aug. 30, 2005 (DK) .................................. 2005 01198

(51) Int. Cl.
*A61F 7/00* (2006.01)
(52) U.S. Cl. ........................................................ 607/114
(58) Field of Classification Search ................ 607/96, 607/104, 107, 108, 109, 110, 111, 112, 114
See application file for complete search history.

(56) References Cited

U.S. PATENT DOCUMENTS

| | | | |
|---|---|---|---|
| 3,889,684 A | | 6/1975 | Lebold |
| 3,951,127 A | * | 4/1976 | Watson et al. ................. 126/206 |
| 4,743,726 A | | 5/1988 | Hughes et al. |
| 5,090,409 A | * | 2/1992 | Genis ............................ 607/108 |
| 5,135,518 A | | 8/1992 | Vera |
| 5,447,531 A | | 9/1995 | Wood |
| 5,447,532 A | | 9/1995 | Furuya |
| 5,709,089 A | * | 1/1998 | Dawson et al. ..................... 62/4 |
| 6,132,454 A | | 10/2000 | Fellows |
| 2005/0261755 A1 | * | 11/2005 | Bacino et al. ................. 607/114 |

FOREIGN PATENT DOCUMENTS

| | | |
|---|---|---|
| CN | 2493183 Y | 5/2002 |
| CN | 2497749 Y | 7/2002 |
| DE | 597664 C | 5/1934 |
| GB | 2290705 A | 1/1996 |
| GB | 2395910 A | 6/2004 |
| JP | 09182764 | 7/1997 |
| NL | 1021279 C2 | 2/2004 |
| WO | 0178797 A1 | 10/2001 |

\* cited by examiner

*Primary Examiner* — Christopher D Koharski
(74) *Attorney, Agent, or Firm* — Muncy, Geissler, Olds & Lowe, PLLC

(57) ABSTRACT

A cushion (1) includes a flexible cover (2) defining a chamber (15). A water-absorbing material (3) is placed inside the chamber, upon absorption of water said water-absorbing material is suitable for heating by means of microwaves. The cover (2) has a sealable feeding mouth (4) so that water may be poured into the chamber (15).

12 Claims, 3 Drawing Sheets

HEAT CUSHION

TECHNICAL FIELD

The present invention relates to a cushion which can be used for heat treatment or cryotherapy, and which is suitable for being heated in a microwave oven.

BACKGROUND ART

Heat cushions or hot water bottles are traditionally made from a thick rubber material constituting a chamber and with an outwardly protruding feeding nozzle so that heated water may be poured into the chamber. After filling in water, the feeding nozzle can be sealed, for instance by means of a screw plug. Such a similar heat cushion is e.g. known from GB 2.290.705 relating to a cushion for the back of the head which may be filled with a heating fluid through a neck. The neck is adapted to receive a sealing body so that the liquid does not run out of the cushion. Said sealing body may for instance be inserted by a screw threat. In an alternative embodiment the liquid is permanently located in the cushion for the back of the head which may be heated in a microwave oven.

U.S. Pat. No. 4,743,726 describes a heating element which can be heated by means of microwaves. The heating element has a flexible cellular core which can absorb water so that the whole core is saturated by water and subsequently can be heated by microwaves. The core is encased in a heat and flame resistant rubber element, which can also be heated by microwaves. This rubber element ensures that the element can be heated to an even higher temperature.

U.S. Pat. No. 5,447,531 relates to a therapeutic heat cushion which is filled with a water-absorbing material containing polyacrylamide. The cushion has an outer layer of material which is water permeable, whereby the cushion can be lowered into water so that the water absorbing material takes up water. Subsequently the cushion can be heated in a microwave oven. The cushion can be dried after use and can be applied several times.

WO/0178797 describes a therapeutic heat cushion the interior of which contains pearls of alumina together with a compound of glycerol and absorbed water. This is sheathed by a cloth with two functionally different surfaces. Thus one side of the cushion is water permeable while the other side is impermeable. Hereby, after heating in a microwave oven, the cushion may be applied either to transfer humid heat or to transfer dry heat.

GB 2.395.910 relates to a heat cushion containing wheat, barley, rice, grain or foam which may be heated in a microwave oven. The cushion has an area adapted to change colour depending on the temperature variations.

U.S. Pat. No. 5,135,518 describes a compress for humid heat treatment. The compress has a water absorbing layer between a liquid impermeable layer and a liquid permeable layer.

Traditional heat cushions which can be filled with heated water have the disadvantage that the pouch may be very "lively" and have a tendency to gather water when the cushion is applied as a heat compress, not achieving a uniform heat supply at the respective place on the body where the compress is used. Furthermore such heat cushions have a tendency to be voluminous. This is also the case for those heat cushions which, via a permanent aqueous core or a grain core are suitable for heating in a microwave oven. Heat cushions having a water absorbing core which are filled by lowering the cushion into water have the disadvantage that they are unhygienic on multiple appliances, as they may gather bacteria in the core, or they may gather several waste products from the human body. Furthermore there is the risk of almost boiling water running out of the cushion and scalding the user.

DISCLOSURE OF INVENTION

The object of the invention is to provide a new and increased heat cushion rectifying the above disadvantages.

This is achieved by means of a cushion including a flexible cover defining a chamber in which a water absorbing material is placed, said water absorbing material upon absorption of water being suitable for heating by means of microwaves, wherein the cover has a sealable feeding mouth so that water may be poured into the chamber. Hereby a heat cushion is obtained which is very compact and light-weight prior to appliance as the water absorbing core can be kept dry. This is an advantage as far as transport and distribution are concerned. Furthermore a sterile transfer of heat is achieved as the core and the water are sheathed by a cover after filling up. Furthermore the cushion can be manufactured from cheap material making the cushion suitable for disposable use, whereby the cushion does not have any of the unhygienic disadvantages of heat cushions for multiple appliances. In addition the cushion needs not to be wiped off prior to use. In some cases, however, it can be necessary to dab the cushion dry. Of course, the heat cushion may also be used to cool down a body part, for instance by filling the cushion with water and putting it in the freezer prior to us.

In a preferred embodiment the water absorbing material with the absorbed water substantially fills the entire chamber. Hereby the heat cushion does not have a tendency to form water gathering when the cushion is used as a heat compression thus ensuring an evenly distributed heat transfer from the heat cushion.

Preferably the cover of the cushion is made from a polymeric film which is resistant to heating by means of microwaves. The cover may for instance be formed by means of two polymeric layers welded together along their circumference. Alternatively the cover may be formed by means of one polymeric layer which is folded and subsequently welded together at the sides. In another embodiment the cover is made from a rubber material.

In a preferred embodiment of the invention the cover is coated with an outer textile layer or sheathed by a textile cushion. Hereby a contact face is obtained which may feel more comfortable for a user using the heat cushion. The outer textile is preferably a thin non-woven material. The non-woven material can be welded together with the polymeric film. The total weight of the flexible cover can thereby be kept low.

In a particular embodiment the water absorbing material is a sponge-like material. Hereby a particularly simple design is obtained of the core of the cushion as the sponge-like material often may absorb a lot of water and swallow up on taking in water, whereby the material may fill the chamber of the whole cushion. The sponge-like material may be coated with a semipermeable membrane to ensure that the water stays in the sponge-like material although said material is exposed to a pressure.

In an alternative preferred embodiment the water absorbing material is a powder material. Preferably said powder lies dry in the cushion prior to usage, and on absorbing water it gains a gel-like viscosity thus achieving an even distribution of the material in the cover of the cushion. It is for instance sufficient to use only 5-10 grams of a super absorbent polymer (SAP) as the powder material in order to achieve an evenly distributed gel-like viscosity after filling in water. If the flexible cover is made from a polymeric film, optionally covered with a non-woven material, the overall weight of a cushion can be kept under 20 grams. This also means that the cushion is very compact in size, making it suitable for sale in multiple packets.

In a preferred embodiment a check valve is provided in connection with the feeding mouth. Hereby a particularly simple sealing mechanism is obtained as the feeding mouth is self-sealing after filling in water.

In another embodiment the feeding mouth is provided in an outwardly protruding feeding nozzle which preferably is sealable by means of a closing body. Said closing body is preferably shaped as a plug or cap adapted to cooperate sealingly with the nozzle, and which preferably has a thread. Hereby an alternative simple sealing mechanism is obtained.

In an alternative embodiment at least two flaps or strings are placed in connection with the feeding mouth on the outside of the cushion. Hereby the feeding mouth can be sealed by tying said flaps or strings together after filling in water. It is also possible to use Velcro or some sort of adhesive tape, for instance the type known from diapers. It is also possible to use hooks which will stick to the non-woven material.

In a preferred embodiment of the cushion, the cushion has a safety valve body opening at a predetermined differential pressure between the pressure inside the cushion and the ambient pressure. Hereby it is ensured that the cover of the cushion does not burst during or immediately after heating the cushion due to an inner excess pressure with the risk of the user being scalded by the hot water.

Preferably the cushion is provided with a temperature indicator, for instance by the cover having an area which changes colour depending on the temperature of the cushion. Thus it can be ensured that, e.g. on therapeutic treatment, the cushion is used when it has the optimum temperature for the therapeutic treatment. At the same time it can also be ensured that the cushion is not used at such a high temperature that the user feels it to be unpleasant.

In one embodiment of the invention the cushion has a first side and an opposite second side, the two sides having different heat transfer characteristics. Thus it can be ensured that one side of the cushion keeps the heat better than the other, whereby, after heating the cushion, first one side of the cushion may be used for the therapeutic treatment until it has fallen to a certain temperature, whereafter the heat cushion is turned and the opposite side is used during the rest of the treatment. The different heat transmission characteristics can for instance be achieved by making the thickness of the cover different at the two sides.

In a preferred embodiment the cushion has perforations allowing the passage of vapour but not water through the cover. Hereby the perforations may be used in the same way as the above excess pressure protection. In a particular embodiment the cushion only has perforations at one side of the cushion. Hereby one may chose between using one side of the heat cushion for "dry" heat treatment or the other side of the heat cushion for humid heat treatment.

The cushion may be formed with a number of strings or flaps adapted to be tied around a body. Hereby the strings may for instance be tied around the thigh of a person, whereby the cushion is kept in its place and there is no need to hold on to the cushion.

The cushion may have many different designs. It may for instance be formed like a sole of a shoe so that the cushion may be used as a heat insole in a shoe. The cushion may also have the form of a seat or a seat pillow being able to be used at e.g. sidewalk cafés or stadium seats where seats may often be cold.

The nursing sector is an area in which the heat cushion is particularly applicable. Here many heat cushions are used, e.g. for wound treatment. Here cheap disposable heat cushions are particularly applicable as sterile, hygienic usage can be ensured and the risk of dissemination can be reduced.

BRIEF DESCRIPTION OF THE DRAWINGS

The invention is explained in detail below with reference to the drawings, in which.

BEST MODES FOR CARRYING OUT THE INVENTION

Figure 1:
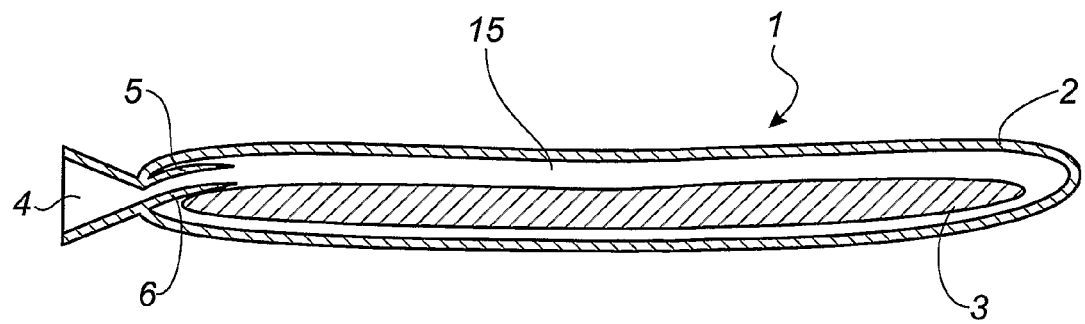
FIG. 1 shows a sectional view through a heat cushion according to the invention with a check valve for filling in water.

FIG. 1 shows a sectional view of a heat cushion 1 according to the invention. The cushion 1 has a cover 2 defining a chamber 15, and which is formed like a thin plastic film. The cushion 1 has an outwardly protruding feeding nozzle 4, which preferably is funnel-shaped so that it easily can be placed on a water tap with a view to filling water into the cushion. Inside the cushion 1 a water absorbing material 3 is placed, preferably in the form of a sponge-like material sheathed with a semi-permeable membrane or in form of a powder material. A check valve with two side walls 5, 6 opposite each other is provided in connection with the feeding mouth 4.

Prior to being filled with water, the heat cushion 1 is totally flat as shown in FIG. 1 and may be folded so that it does not take up much space. The cheap material makes the cushion 1 particularly suitable for disposable usage and not taking up much space makes the cushions 1 suitable for sale in multiple packets of for instance ten disposable heat cushions.

Upon filling in water a plastic pipe may for example be inserted into the feeding mouth 4 ensuring that the side walls 5, 6 placed opposite each other and thus the check valve are kept open during the fill-up. The cushions may for instance be sold with inserted plastic pipes. Alternatively the water pressure from filling in water will be sufficient to keep the check valve open.

Figure 2:
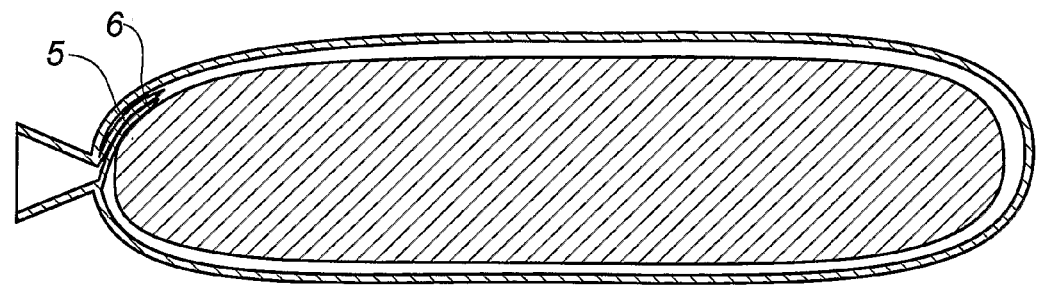
FIG. 2 shows the heat cushion according to the invention shown in FIG. 1 with a check valve after filling in water.

Concurrently with the heat cushion 1 being filled up, the water absorbing material 3 absorbs water and swallows up finally substantially filling up the chamber 15 of the entire cushion 1. Subsequently the plastic pipe, if used, is pulled out of the feeding mouth 4 whereupon the side walls 5, 6 of the check valve are pressed together by the interior water pressure of the cushion 1 or by the sponge-like material 3 abutting the check valve as shown in FIG. 2.

After the water has been filled in, the cushion 1 can be put in a microwave oven and the aqueous core consisting of the sponge-like material 3 can be heated. Hereupon the cushion 1 can be put on the place on the body on which the heat treatment is desired. Alternatively, the cushion 1 can be put into a freezer until the temperature desired for the cushion 1 has been reached if the cushion 1 is to be used for cooling.

Figure 3:
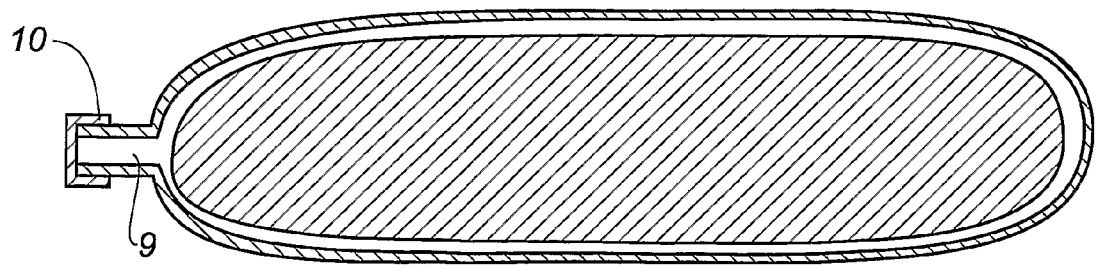
FIG. 3 is a sectional view through a heat cushion according to the invention filled with water with an outwardly protruding feeding nozzle and a cap.

An alternative embodiment of the heat cushion 1 is shown in FIG. 3. Here the heat cushion is provided with an outwardly protruding feeding nozzle 9 with an outer thread. After filling in water, the feeding nozzle is closed by sealingly screwing on a cap 10.

In a particularly preferred embodiment, the water absorbing material 3 is a super absorbent polymer (SAP) in powder form. After filling in water, the SAP powder absorbs the water and generates a gel like viscosity. 5-10 grams of SAP powder are sufficient to generate an even distribution of gel in the chamber 15. In order to ensure that the SAP powder is evenly distributed in the chamber 15, the SAP powder can be distributed in lines on a thin sheet of paper, said paper dissolving after the filling of water. If the flexible cover is made from a polymeric film, optionally covered with a non-woven material, the overall weight of a cushion can be kept under 20 grams. This means that the cushion 1 is very compact in size and the material costs are low, making the cushion 1 suitable for sale in multiple packets.

Figure 4:
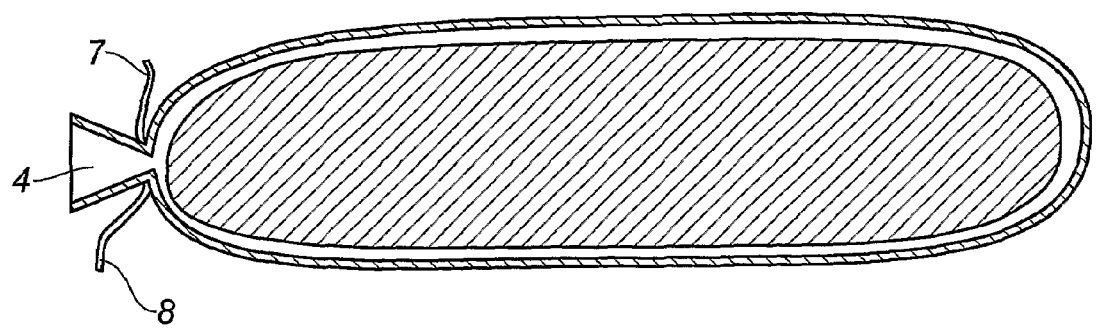
FIG. 4 is a sectional view through a heat cushion according to the invention filled with water with flaps placed in connection with the feeding mouth of the cushion.

As shown in FIG. 4, in another embodiment the heat cushion 1 is provided with two strings or flaps 7, 8 in connection with the feeding mouth 4. After filling in water, said strings or flaps can be tied together so that the feeding mouth 4 is closed.

Figure 5:
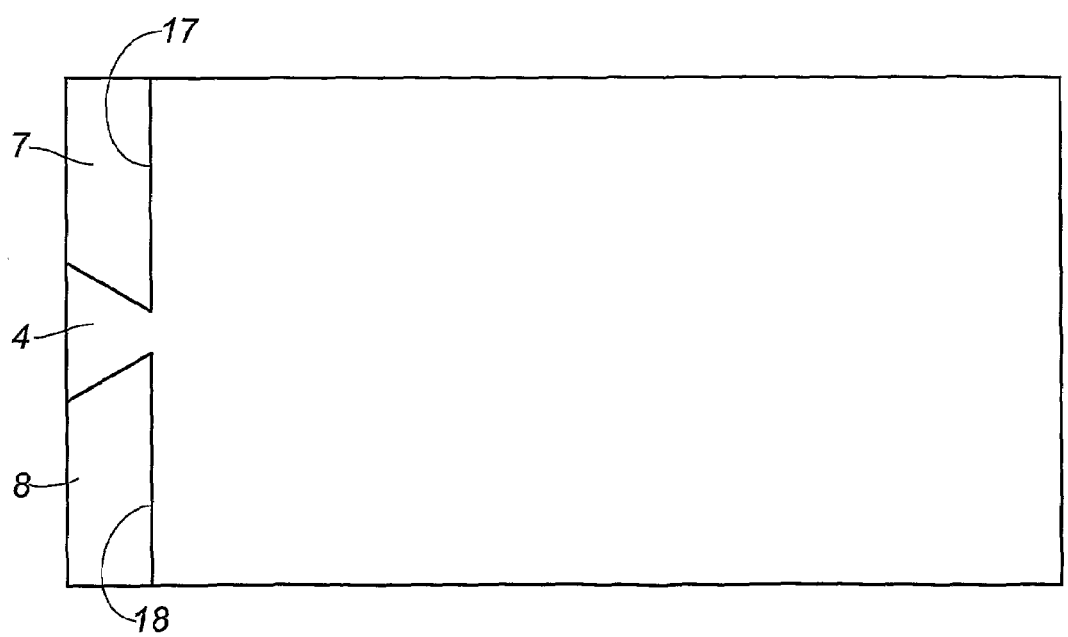
FIG. 5 is a schematic presentation of an alternative embodiment of the heat cushion with flaps placed in connection with the feeding mouth of the cushion, seen from above.

Another way of providing the feeding mouth with two strings 7, 8 is shown in FIG. 5, which shows the heat cushion 1 from above. Here the strings 7, 8 are formed by welding along the lines 17, 18, the strings 7, 8 being able to be torn off along said lines 17, 18. Subsequently the strings 7, 8 can be tied together to seal the feeding mouth 4. The cushion 1 may of course still be provided with a check valve, the strings 7, 8 only serving as an additional protection ensuring that no water runs out of the feeding mouth 4.

Figure 6:
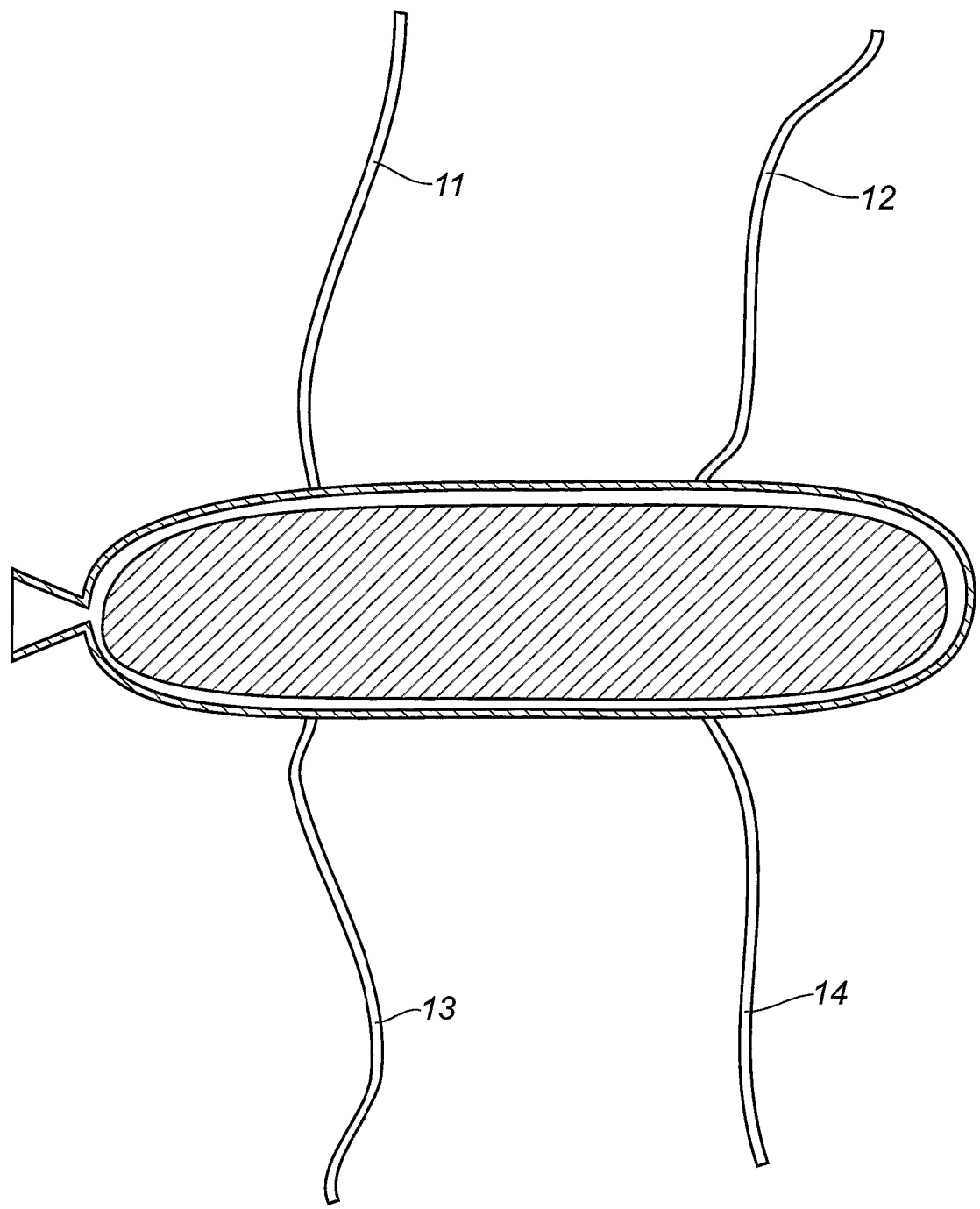
FIG. 6 is a sectional view through a heat cushion according to the invention filled with water with strings adapted to be tied around a body part.

As shown in FIG. 6 the heat cushion may be provided with a number of strings or laces 11, 12, 13, 14 by means of which the heat cushion 1 for instance may be tied around the thigh of a person needing heat treatment. In this way the heat cushion 1 stays in the place in which the heat treatment is required and the heat cushion 1 need not be held on to. It is also possible to use Velcro or some sort of adhesive tape, for instance the type known from diapers. It is also possible to use hooks which will stick to the non-woven material.

The heat cushion 1 may be formed with two sides with different thicknesses so that these sides have different heat transmission characteristics. Thus first one side of the heat cushion 1 may advantageously be used for heat treatment and then the second side of the heat cushion 1 may be used when the temperature of the first side has dropped to a certain value. The two sides of the heat cushion 1 may have different colours to show which side to start with during the heat treatment. Alternative the two sides may have an area with for instance a medium depending on temperature, such as ink, changing colour depending on the temperature or another way of indicating the temperature.

The nursing and hospital sectors are areas in which the heat cushion 1 is particularly applicable. Here, due to the low cost price the cushion 1 may be disposed of after use. Thus high hygiene can be ensured so that patients with bedsore or infectious disease can be given heat treatment without the risk of spreading infection. Almost all wards have access to a microwave oven now just as there is a microwave oven in almost every ward/apartment at residential homes. Hereby the cushion can easily be heated. At present, most often gel holding heat cushions are the alternative. Such gel holding heat cushions need to be warmed up in boiling water prior to use resulting in much time consumption for nurses and inconveniences due to having to handle wet cushions in large pots with subsequent wiping off etc. The risk of spreading infection from for instance wounds is greatly increased as well, as the heat cushions need to be transported from the wards to for instance the wash room after use where they have to be sterilised and re-heated. An advantage of the heat cushion 1 according to the invention is that it only needs to be handled prior to use when everything is sterile and without the risk of infection as only water from the tap is used.

The heat cushion 1 can also be used in cribs where the heat cushion may be placed prior to putting down the baby so that the bed is warm.

As mentioned the heat cushion 1 is cheap and its compact size makes it suitable for sale in multiple packets. This may for instance be interesting for long-distance truckers or in connection with car holidays. Thus if the body aches in different places after a long drive it is possible to for instance stop at a filling station, take a heat cushion 1 from the multiple packet and then fill it with water and finally heat it in the microwave oven of the filling station. Hereafter the cushion 1 can be used to soothe the aching muscles. In that connection the heat cushion 1 may for instance be formed like a cushion for the back of the head.

The cushion 1 may also have the shape of a sole of a shoe so that it can be used as a disposable insole in shoes.

The compact heat cushions 1 may also be interesting for sidewalk cafés or other public houses. Here the heat cushion 1 may be shaped like a seat or a seat cushion, and then the public house may offer its customers a heated cushion 1 to sit on in order to keep warm better. Here the sitting cushions can be sold cheaply or given away free to attract customers or printed with sponsor logos, commercials etc. The heated sitting cushions are also interesting in connection with soccer games or similar stadium events where spectators often sit down for hours and as the stadiums often are made of concrete this may be a cold experience, particularly during the winter months.

The invention has been described with reference to preferred embodiments. Many changes may be made without hereby diverting from the idea behind the invention. Modifications and variations which are obvious to a person skilled in the art are considered to be covered by the scope of the present invention.

The invention claimed is:

1. A heat cushion comprising:
   a flexible cover defining a chamber in which a water absorbing material is placed, said water absorbing material upon absorption of water being suitable for heating by means of microwaves;
   a sealable feeding mouth formed on the flexible cover so that water may be poured into the chamber; and
   a check valve provided in connection with the feeding mouth;
   wherein the water absorbing material is a powder material of super absorbent polymer (SAP), and wherein the flexible cover is made from a polymeric film covered with a textile, and wherein the cushion comprises a safety valve body opening at a predetermined differential pressure between the pressure inside the cushion and the ambient pressure, the pressure inside the cushion being higher than the ambient pressure.

2. The cushion according to claim 1, wherein the check valve is formed integrally with the flexible cover.

3. The cushion according to claim 1, wherein the check valve in connection with the feeding mouth allow water to be poured into the chamber and inhibit water from exiting the chamber.

4. The cushion according to claim 1, wherein the check valve comprises two flaps, each flap disposed generally on opposite sides of the feeding mouth.

5. The cushion according to claim 4, wherein pressure from the water presses the flaps together, thus inhibiting water from exiting the chamber.

6. The cushion according to claim 1, wherein the water absorbing material with the absorbed water substantially fills the whole chamber.

7. The cushion according to claim 1, wherein the feeding mouth is provided in an outwardly protruding feeding nozzle preferably sealable by a closing body.

8. The cushion according to claim 7, wherein the closing body is a plug or cap adapted to cooperate sealingly with the nozzle, and which preferably has a thread.

9. The cushion according to claim 1, wherein at least two flaps or strings are placed in connection with the feeding mouth on the outside of the cushion.

10. The cushion according to claim 1, wherein the cushion has a first side and an opposite second side, the two sides having different heat transfer characteristics.

11. The cushion according to claim 1, wherein the flexible cover is covered with a non-woven textile.

12. The cushion according to claim 11, wherein the non-woven textile is joined to the flexible cover, for instance by welding.

* * * * *